United States Patent [19]

Rajala et al.

[11] Patent Number: 4,915,767
[45] Date of Patent: Apr. 10, 1990

[54] APPARATUS FOR APPLYING AN ELASTIC IN A CURVED PATTERN TO A MOVING WEB

[75] Inventors: Gregory J. Rajala, Neenah, Wis.; William J. Moore, Brea, Calif.; Kurt J. Kloehn, Little Chute, Wis.

[73] Assignee: Kimberly-Clark Corporation, Neenah, Wis.

[21] Appl. No.: 272,670

[22] Filed: Nov. 17, 1988

[51] Int. Cl.⁴ .................. A61F 13/16; B32B 31/08; A41B 13/02
[52] U.S. Cl. .................................. 156/440; 156/161; 156/164; 156/229; 156/436; 156/439; 156/494; 156/495
[58] Field of Search ............... 156/161, 164, 440, 555, 156/495, 494, 436, 439, 160, 177, 229; 226/179; 604/385.2

[56] References Cited

U.S. PATENT DOCUMENTS

| | | |
|---|---|---|
| 2,592,581 | 1/1950 | Lorig . |
| 3,761,341 | 9/1973 | Kimble .............. 156/177 X |
| 3,828,367 | 8/1974 | Bourgeois ................. 2/224 |
| 4,081,301 | 3/1978 | Buell ................. 156/164 |
| 4,227,952 | 10/1980 | Sabee ................. 156/164 |
| 4,293,367 | 10/1981 | Klasek et al. ........... 156/494 |
| 4,300,967 | 11/1981 | Sigl ................... 156/164 |
| 4,600,456 | 7/1986 | Oswald ............ 156/440 X |
| 4,675,068 | 6/1987 | Lundmark ............ 156/164 X |
| 4,726,873 | 2/1988 | Ales et al. ............. 156/495 |
| 4,801,345 | 1/1989 | Dussaud et al. .......... 156/164 |

OTHER PUBLICATIONS

Serial Number 06/621,900 filed 6-18-84 to Kons entitled "Method and Apparatus for Applying Elastic Ribbon to a Web Along an Undulated Path".

Primary Examiner—Michael W. Ball
Assistant Examiner—Jeff H. Aftergut
Attorney, Agent, or Firm—Douglas L. Miller

[57] ABSTRACT

An apparatus (10) of the type for applying an elastic ribbon (18) onto the surface of a moving web (12) in curved line path relative to the longitudinal centerline (14) of the web (12) includes a nip roll (16) for directly rolling the elastic ribbon (18) into engagement with the moving web (12) and an oscillating roll (20) adjacent to and spaced from the nip roll (16) for oscillatiang the elastic ribbon (18) in a direction transverse the centerline of the web (12) and applying the elastic ribbon (18) to the nip roll (16) in the curved line path. A guide roll (22) guides the elastic ribbon (18) to wrap around the oscillating roll (20) and tension the elastic ribbon sufficiently for tracking and holding the lateral position of the elastic ribbon (18) on the nip roll (16) to be applied to the moving web (12) in the curved line path.

8 Claims, 2 Drawing Sheets

FIG. I

APPARATUS FOR APPLYING AN ELASTIC IN A CURVED PATTERN TO A MOVING WEB

TECHNICAL FIELD

This invention relates to a method and apparatus for applying elastic ribbon to a web along a curved or undulated path and, in particular, to fabricating disposable garments such as disposable diapers having curved elastic in their leg areas.

BACKGROUND OF THE INVENTION

There has a been a trend in the field of disposable diaper manufacturing to improve leakage prevention while making the disposable diaper appear and fit more like the undergarments they are meant to replace. This goal is best achieved by a disposable diaper with curved leg elastics.

Curving the leg elastics has been very difficult to accomplish and practice at high speed. Manufacturers have settled for making disposable diapers having straight bands of elastic.

The application of an elastic in a steeply curved pattern to a moving web requires the use of rollers for positioning the strip of elastic. U.S. Pat. No. 2,592,581 to Lorig discloses a method and apparatus for positioning a strip utilizing a roll which may be cylindrical, concave, or convex as desired to suit various installations. The U.S. Pat. No. 4,081,301 to Buell and U.S. Pat. No. 4,227,952 to Sabee disclose typical arrangements for applying elastic along a straight line to a web. In the Buell patent, the elastic and web substrate are continuously run at high speed while adhesive is intermittently applied to the elastic material.

The U.S. Pat. No. 3,828,367 Bourgeois discloses an apparatus for applying curved elastic to a disposable garment In the Bourgeois patent, a pair of elastic ribbons are fed to curved grooves in a roll under which a continuous web passes. As the roll with the ribbons in its grooves goes over the web, the ribbons are transferred in the contoured pattern of the grooves to the roll. One problem with a grooved roll for applying elastic ribbon to a web is that a groove which is sufficiently deep to guide the ribbon is too deep to apply a flat elastic ribbon. A curved groove is unreliable insofar as preventing roping and C-folding of a flat ribbon.

The U.S. patent application Ser. No. 621,900, filed June 18, 1984 and assigned to the assignee of the present application discloses a method and apparatus for applying elastic ribbon to a web along undulated path. The method and apparatus involve a single roll moving or oscillating in a single dimension to apply each elastic ribbon.

The present invention provides an improved means for applying elastic in a moderately steep curved pattern to a moving web using an applicator roll which oscillates in a direction transverse to the direction of the web and whose axis is parallel to the surface thereof. Due to space limitations, a horizontally oriented roll is necessary in order to obviate twisting of the elastic ribbon. Further, the coefficient of friction between the elastic ribbon and the surface of the oscillating roll bears a relationship to the transverse distance over which the roll oscillates in order to apply elastic having a moderately sharp degree of curvature.

SUMMARY OF THE INVENTION

An apparatus for applying an elastic member in a curved path relative to its dwell line onto a continuously moving web comprising a rotatable nip roll being in rolling engagement with the web and pressing the curved elastic member against the web such that the elastic member is spaced a predetermined maximum distance from the dwell line. A rotatable buffer roll is above and in rolling engagement with the nip roll to cushion the nip roll against transient perturbations and to press the curved elastic member against the nip roll to maintain the elastic member in its curved form. An oscillating roll is disposed above and spaced apart a predetermined length from the buffer roll. The oscillating roll oscillates in a path generally transverse to the direction of web travel and applies the elastic member in a curved line on the buffer roll. The predetermined maximum distance of the elastic member from the dwell line is directly proportional to the predetermined length between the oscillating roll and the buffer roll.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
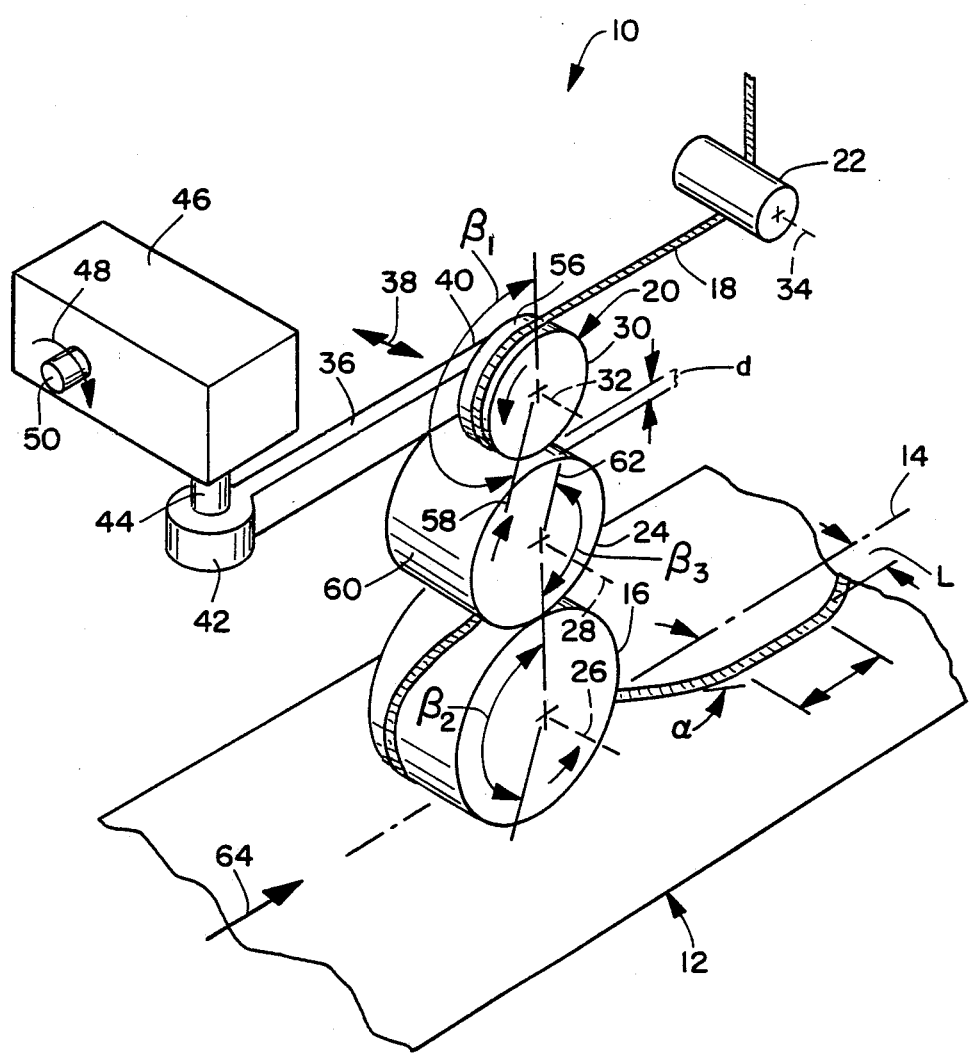
FIG. 1 is a perspective view of the present invention.

An apparatus of the type for applying an elastic ribbon on the surface of a moving web in a curved line path relative to a longitudinal centerline of web constructed in accordance with the present invention is generally shown at 10 in the Figures. The moving web, generally shown at 12, includes a longitudinal centerline or dwell line 14.

The apparatus 10 generally includes nip roll means 16 for directly rolling a length of elastic ribbon 18 into engagement with the moving web 12. Oscillating roll means generally indicated 20 is disposed adjacent to and spaced from the nip roll means 16 for oscillating the length of elastic ribbon 18 in a direction transverse to the centerline 14 of the web 12 and applying the elastic ribbon 18 to the nip roll means 16 in the curved line path. Guide roll means 22 guides the elastic ribbon 18 to wrap around the oscillating roll means 20 and tension the elastic ribbon sufficiently for tracking and holding the lateral position of the elastic ribbon 18 on the nip roll means 16 to be applied to the moving web 12 in the curved line path. Stay roll means 24 holds the elastic ribbon 18 on the nip roll means 16 and buffers the nip roll means 16 from perturbations in the elastic ribbon 18.

More specifically, the nip roll means includes a nip roll 16 having a first axis of rotation 26. The stay roll means includes a stay roll 24 having an axis of rotation 28. The oscillating roll means includes an oscillating roll 30 having an axis of rotation 32. The guide roll means includes a guide roll 22 having an axis of rotation 34. The axes 26, 28, 34 are parallel relative to each other.

The oscillating roll 30 is mounted on a pivoting arm 36 which pivots the oscillating roll 30 on a curved path indicated by arrows 38 relative to the longitudinal centerline 14. The oscillating roll 30 has a neutral dwell line wherein the axis of rotation 32 is parallel to the other mentioned axes 26,28,34 whereby the oscillating roll 30 applies the elastic ribbon 18 to the stay roll 24 in a single straight dwell line in the neutral position and in a continuous curvature when moved from the neutral position. In other words, the oscillating roll 30 moves along an arc 38 relative to the fixed rolls 16,22,24. The oscillating roll 30 oscillates in an arcuate path. When the oscillating roll 30 is in a neutral position wherein the axis of rotation 32 is parallel to the axes 26,28,34, the oscillating roll 30 directs the ribbon 18 onto the stay roll 24 in a straight line path. As the oscillating roll 30 is moved by the arm 36, the oscillating roll 30 applies the elastic ribbon 18 onto the stay roll 24 in a continuous curvature.

Figure 2:
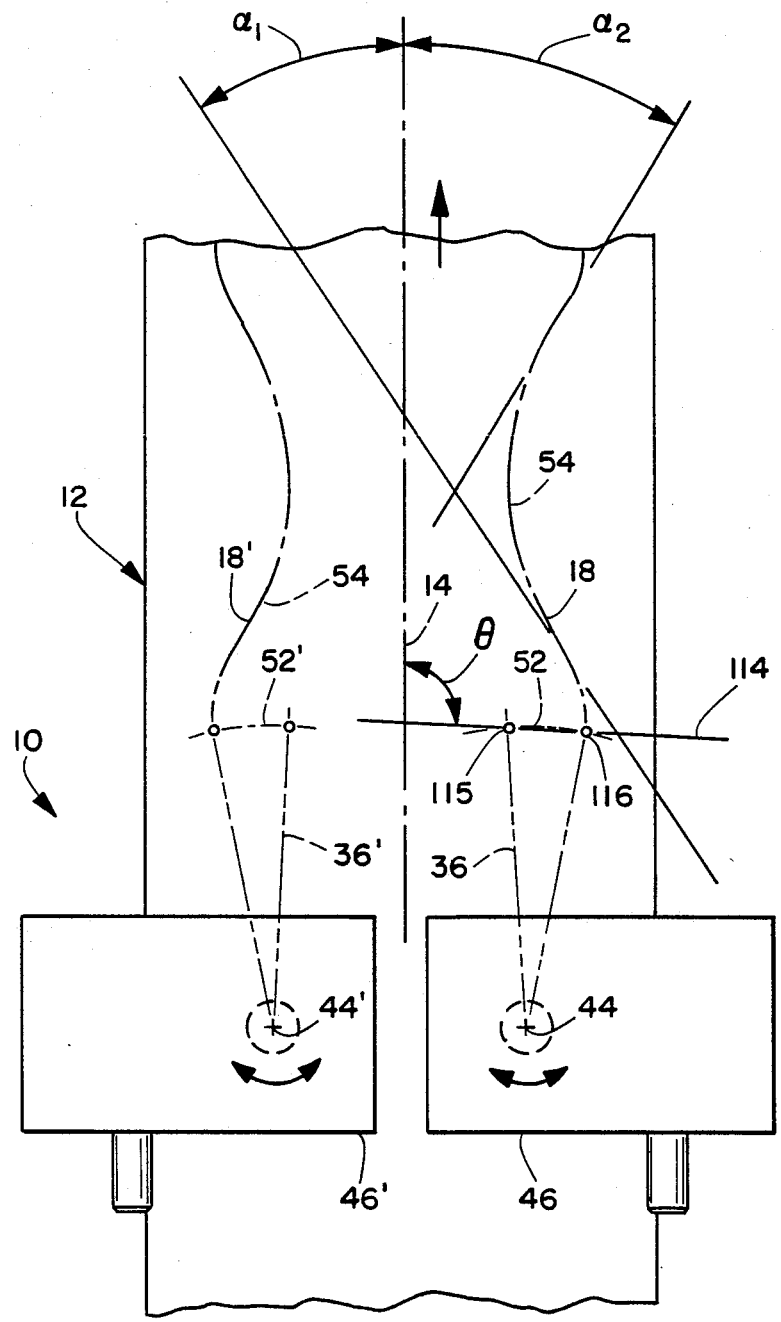
FIG. 2 is a plan view of the applied ribbon path of the invention, illustrating the critical deeply curved pattern of the ribbon applied to the moving web.

The oscillating roll 30 is mounted for rotational movement on an end portion 40 of arm 36. The oscillating motion of the arm 36 results from the arm 36 having a second end portion 42 fixedly mounted to an output or follower shaft 44 of a conjugate cam mechanism control 46. This cam mechanism 46 takes a continuous rotary motion as an input, the rotary motion indicated by arrow 48 about rotary shaft 50 and provides a programmed oscillatory motion as an output. For any position of the input shaft 50, the output shaft 44 and arm 36 take a predetermined angular position relative to the centerline 14. The motion of the cam mechanism 46 can be mechanically tied into the movement of the web 12. In FIG. 2, the assembly 10 includes two control cam mechanisms 46,46'. Arms 36,36' extend from output shafts schematically shown at 44,44'. Arm movement is shown about arcs 52,52, The hatched lines 54 indicate the elastic pattern which results when the timed back and forth motion of the oscillating arm is summed with the movement of the web 12.

The present invention provides for a specific orientation of the rolls 16,20,22,24 in order to provide for the application of the elastic ribbon 18 at a maximum curvature upon the web 12 while preventing slippage of the elastic ribbon 18 on the rolls 16,24 as they are disposed thereon and further preventing C-folding of the flat elastic ribbon 18.

To accomplish the aforementioned goals, the nip roll 16 is configured in such a way that the elastic ribbon 18 is pressed against the web 12 by a controllable amount of force. The stay roll 24 is disposed adjacent the nip roll 16 to hold the elastic ribbon to the nip roll 16 and also serves to buffer the nip roll from perturbations which are occurring in the elastic ribbon upstream from the nip roll 16. The guide roll 22 guides the elastic ribbon 18 to the oscillator roll 30 and insures a sufficient elastic wrap angle on the oscillator roll 30. The wrap angle is indicated in FIG. 1 as $\beta_1$. The lateral position of the elastic ribbon 18 on the nip roll 16 and stay roll 24, as deviated from the centerline 14 by the oscillating roll 30, determines where the elastic ribbon 18 is placed on the moving web 12.

The elastic ribbon 18 has a contact friction dependent upon the surface texture and adhesion of the elastic ribbon 18 relative to the receiving surface 56 of the oscillating roll 30. The elastic ribbon 18 also has an angle of wrap $\beta_1$ on the oscillating roll as defined above. The contact friction and angle of wrap of the elastic ribbon on the oscillating roll 30 is determined by the relative fixed position of the guide roll 22 and stay roll 24 to the oscillating roll, thereby determining the wrap angle $\beta_1$ about the oscillating roll 30. Similarly, the relative fixed position of the stay roll 24 to the nip roll 16 and oscillating roll 30 determines the wrap angles $\beta_2$ and $\beta_3$ of the elastic about the nip roll 16 and stay roll 24. The tangent lines are the path line of the elastic ribbon 18 tangent to the annular outer surface of each roll 16,24,30. Each incoming and outgoing tangent path line for each roll 16,24,30 defines a wrap angle $\beta_1$, $\beta_2$ and $\beta_3$ expressed in radians for each roll 16,24,30, as shown in FIG. 1. Each roll has a predetermined coefficient of friction $\mu$. The friction and angle of wrap of the elastic ribbon on the oscillating roll 30, stay roll 24, and nip roll 16 govern to a great extent the maximum angle that the elastic can make to the centerline 14 of the web 12. The maximum angle indicated at $\alpha$ in FIGS. 1 and 2 is an angle wherein, $\alpha = \arctan \mu\beta$.

Depending upon the roll, $\beta$ can equal $\beta_1$ with regard to the oscillating roll 30 and $\beta_2$ with regard to the nip roll 16 and $\beta_3$ with regard to the stay roll 24. The wrap angle $\beta_2$ around the nip roll 16, stay roll 24, and oscillating roll 30, are at least 30°. The angle which the elastic ribbon 18 can make to the centerline 14 of the web has a practical limit of about 60°.

The elastic ribbon 18 is displaced from the centerline 14 distance L when the elastic ribbon 18 is deviated at a maximum angle from the centerline 14. The oscillating roll 30 has a circumferential surface intersecting the outgoing tangent path thereof at a first tangency point 58. That is, because of the spacing indicated at d between the oscillating roll 30 and stay roll 24, the elastic ribbon leaves the receiving surface 56 of the oscillating roll at point 58. The stay roll 24 has a circumferential surface 60 intersecting the incoming tangency path of the elastic ribbon 18 at point 62. The tangency points 58,62 are spaced apart less than the distance d wherein $$d = \frac{L}{\tan \alpha}$$

in order to allow, in conjunction with the coefficient of friction and wrap angle relationship formulated above, the maximum displacement of the elastic ribbon 18 relative to the centerline 14. To obtain maximum efficiency from the system the guide roll 22 and oscillating roll 30 are separated by a distance greater than 5d.

The pivoting arm 36 has an optimum length range from about 4 to 10 inches in length, preferably 6 to 7 inches in length. The elastic ribbon will C-fold if its width to thickness ratio is less than about 7. Preferably, the ratio should be greater than about 14 to 16.

An adhesive elastic, such as Fullastic ® or an elastic ribbon of either Tuftane ® or natural rubber coated on both sides with a pressure sensitive adhesive is preferred in the process. The adhesive enhances the coefficient of the friction of the material and lowers the materials tendency to C-fold.

The preferred location for the output shaft 44 from the oscillating roll 30 is upstream of the flow of the web 12, the flow of the web being shown by arrow 64. This location has been found to yield the best cam life.

The desired path over which the elastic ribbon follows can be characterized by two important angles $\alpha 1$ and $\alpha 2$, as shown in FIG. 2. These are the maximum angles that tangents to the elastic ribbon curve make with the centerline 14 of the web 12. The end portion 40 of arm 36 has an optimum path for oscillating back and forth motion being substantially along a line 114 at an angle θ relative to the centerline 14 wherein $$\theta = \arctan 2 \frac{\tan(-\alpha_1)\tan\alpha_2}{\tan\alpha_2 + \tan(-\alpha_1)}$$

Taking a segment of the slope line 114 between the extremes of the arm motion 115;116, the center of the output shaft 44 of the arm 36 must be substantially on the perpendicular bisector of this line segment.

The tension of the ribbon 18 is not critical if the coefficient of friction and wrap are high enough to allow for an angle α. The elastic ribbon 18 will make the angle α at all tensions. The friction force results from the normal force and the friction coefficient. A higher elastic web tension creates a greater sideways force on the displaced elastic ribbon 18, but this is compensated by the increased normal force and frictional force.

The direction of motion at the top of the stay roll 24 is the same as web 12 so that the elastic pattern seen developing on the stay roll 24 is the same as the pattern on the web 12. Accordingly, the oscillator roll motions are easier to monitor off the stay roll 24 as the elastic ribbon 18 is being applied. The stay roll 24 further buffers the nip roll 16, that is, the elastic that is applied on it is not being moved which helps to stabilize the elastic ribbon. The stay roll 24 further functions as a one way free running clutch in that the stay roll is adapted to rotate in only one direction. Thusly, if the elastic breaks after the stay roll, the one way clutch keeps the stay roll 24 from rotating backwards under the influence of upstream web tension thereby preventing unthreading of the elastic ribbon 18.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An apparatus for applying an elastic member in a curved path relative to its dwell line onto a continuously moving web, comprising:
   a rotatable nip roll adapted to be in rolling engagement with the web and to press an elastic member against the web such that the elastic member is spaced a predetermined maximum distance from the dwell line,
   a rotatable buffer roll being disposed above and in rolling engagement with said rotatable nip roll to cushion said rotatable nip roll against transient perturbations and being adapted to press the elastic member against said rotatable nip roll to maintain the elastic member in a curved form, and
   an oscillating roll being disposed above and spaced apart a predetermined length from said rotatable buffer roll, said oscillating roll oscillating in a path generally transverse to a direction of web travel and applying the elastic member in a curved line on said rotatable buffer roll,
   the predetermined maximum distance of the elastic member from the dwell line being directly proportional to the predetermined length between said oscillating roll and said rotatable buffer roll.

2. The apparatus of claim 1 further comprising a tensioning guide roll spaced apart from said oscillating roll and adapted to deliver the elastic member under a predetermined tension to said oscillating roll.

3. The apparatus of claim 2 wherein a contact friction angle of wrap of the elastic member on said oscillating roll is determined by the relative fixed position of said guide roll and said buffer roll to said oscillating roll and defining an incoming tangent path line of the elastic member and an outgoing tangent path line of the elastic member from said oscillating roll, the relative position of said oscillating roll, said buffer roll, and said nip roll defining ingoing and outgoing tangent path lines from said buffer roll and said nip roll, said incoming and outgoing tangent path lines for each said roll defining wrap angles $\beta_1$, $\beta_2$, and $\beta_3$ expressed in radians for each of said rolls, each of said rolls having a predetermine coefficient of friction μ wherein the maximum angle that the elastic member can make to the dwell line being an angle α defined by the formula:

$$\alpha = \arctan\mu\beta$$

4. The apparatus of claim 12 wherein said wrap angles $\beta_1$, $\beta_2$, and $\beta_3$ around said nip roll, said buffer roll, and said oscillating roll β are at least 30°.

5. The apparatus of claim 4 wherein the maximum angle between the curved elastic member and the dwell line is an angle α;
   and wherein the predetermined maximum distance L of the curved elastic member from the dwell line, the predetermined distance d between said oscillating roll and said buffer roll, and maximum angle α are related as follows:

$$d = L/\tan\alpha$$

6. The apparatus of claim 5 wherein said guide roll and said oscillating roll are spaced apart a distance of at least about 5d.

7. The apparatus of claim 6 wherein the continuous curvature of the curved elastic member relative to the dwell line defines two maximum angles $\alpha_1$ and $\alpha_2$ between the tangents to the curvature relative to the dwell line, the elastic member having an optimum path for maximum oscillating back and forth curvature being substantially along a line at an angle β relative to the dwell line wherein $$\theta = \arctan 2 \frac{\tan(-\alpha_1)\tan\alpha_2}{\tan\alpha_2 + \tan(-\alpha_1)}.$$

8. The apparatus of claim 1 wherein said oscillating roll is attached to a pivot arm having a pivot axis upstream of the direction of web travel.

* * * * *

UNITED STATES PATENT AND TRADEMARK OFFICE
CERTIFICATE OF CORRECTION

PATENT NO. : 4,915,767  
DATED : April 10, 1990  
INVENTOR(S) : Gregory J. Rajala, William J. Moore and Kurt J. Kloehn It is certified that error appears in the above-identified patent and that said Letters Patent is hereby corrected as shown below:

Column 3,  
Line 36, insert -- ' -- after the second appearance of "52".

Column 4,  
Line 21, delete "βcan" and substitute -- β can --.  
Line 30, insert -- χ -- after "angle".  
Line 47, insert -- χ -- after "displacement".

Column 6,  
Line 25, delete "predetermine" and substitute -- predetermined --.  
Line 34, delete "β".  
Line 55, delete "β" and substitute -- Θ --.

Signed and Sealed this

Eighth Day of October, 2002

Attest:

Attesting Officer

JAMES E. ROGAN  
Director of the United States Patent and Trademark Office